(12) United States Patent
Andle

(10) Patent No.: US 7,219,537 B2
(45) Date of Patent: May 22, 2007

(54) CONTROL OF EQUIVALENT SHEAR RATE IN ACOUSTIC WAVE SENSORS

(75) Inventor: Jeffrey C Andle, Westbrook, ME (US)

(73) Assignee: Vectron International, a division of Dover Electronics, Inc., Hudson, NH (US)

(*) Notice: Subject to any disclaimer, the term of this patent is extended or adjusted under 35 U.S.C. 154(b) by 0 days.

(21) Appl. No.: 11/382,471

(22) Filed: May 9, 2006

(65) Prior Publication Data
US 2006/0191570 A1    Aug. 31, 2006

Related U.S. Application Data

(60) Continuation-in-part of application No. 11/313,029, filed on Dec. 19, 2005, now Pat. No. 7,181,957, which is a division of application No. 10/743,986, filed on Dec. 22, 2003, now Pat. No. 7,007,546.

(51) Int. Cl.
*G05D 11/00* (2006.01)
*G01N 11/10* (2006.01)

(52) U.S. Cl. .................. 73/54.41; 73/54.01; 73/54.24; 73/54.25; 73/54.27

(58) Field of Classification Search ............... 73/53.01, 73/54.01, 54.24, 54.25, 54.27, 54.41, 61.79, 73/64.53
See application file for complete search history.

(56) References Cited

U.S. PATENT DOCUMENTS

| | | | |
|---|---|---|---|
| 3,712,117 A | 1/1973 | Fitzgerald et al. | |
| 3,903,732 A | 9/1975 | Rork et al. | |
| 5,235,235 A | 8/1993 | Martin et al. | |
| 5,750,884 A | 5/1998 | Field | |
| 5,877,411 A | 3/1999 | Namerikawa et al. | |
| 6,260,408 B1 | 7/2001 | Vig et al. | |
| 6,357,281 B1 | 3/2002 | Wilhelm | |
| 6,439,034 B1 | 8/2002 | Farone et al. | |
| 6,543,274 B1 | 4/2003 | Herrmann et al. | |
| 7,002,281 B2 | 2/2006 | Andle | |
| 2002/0124634 A1 | 9/2002 | Litton | |

*Primary Examiner*—Daniel S. Larkin
(74) *Attorney, Agent, or Firm*—Shalom Wertsberger; Saltamar Innovations

(57) ABSTRACT

An apparatus and a method for controlling the shear rate at which an acoustic wave device measures viscosity, by utilizing an automatic level control or an automatic gain control circuit to control power input to the sensor as a function of the sensor's output power. Further improvement is provided by measuring the input power and combining the input power and output power measurements, preferably by averaging, to control the input power to the sensor. A method is also provided for characterizing the fluid under test by providing a set of viscosity measurements at various shear rates.

14 Claims, 4 Drawing Sheets

CONTROL OF EQUIVALENT SHEAR RATE IN ACOUSTIC WAVE SENSORS

RELATED APPLICATIONS

This application is a continuation in parts of U.S. application Ser. No. 11/313,029, filed Dec. 19, 2005 now U.S. Pat. No. 7,181,957, which is divisional application of, U.S. patent application Ser. No. 10/743,986 filed Dec. 22, 2003, presently issued as U.S. Pat. No. 7,007,546. This application claims the benefit of priority to both of the above applications, which are incorporated herein by reference.

FIELD OF THE INVENTION

This application is directed generally to acoustic wave sensors employing sound waves to measure viscoelastic properties of a material, and more particularly to methods of relating viscosity measurements to the shear rate at which such measurements are performed.

BACKGROUND OF THE INVENTION

Viscosity, and more generally, viscoelasticity, are properties of liquids and solids that relate the shear forces generated by or applied to a material to the amount of shear deformation or flow. While the invention applies equally well to viscoelasticity, the present discussion will be limited to viscosity measurement for simplicity. Viscosity is of widespread interest in many manufacturing environments and is measured as a primary quality of some products and as a secondary quality (a means of monitoring process state) in other processes.

Viscosity describes the force required in order to make successive molecular layers of a liquid move past each other at a given rate of shear ("shear rate"). If one considers a liquid flowing past the walls of a container, the liquid will ideally have no motion relative to the wall at the interface and will have increasingly higher velocities as one observes points successively further from the wall. The shear rate is defined as the gradient of the velocity of the liquid parallel to the surface (meters per second) with increasing distance from the surface (meters). The units of shear rate are 1/seconds. The shear stress is the amount of force per unit area that must be applied in order to cause the motion. While the fluid may have a characteristic flow (and thus a characteristic shear rate) or may be stationary, all measurements of viscosity to date are based on the measurement of shear stress vs. shear rate under an imposed motion of the fluid. Throughout this disclosure, "shear rate at which the viscosity of a fluid" should be taken to mean the shear rate at which the viscosity of the fluid is measured, which may differ substantially from the characteristic shear rate of the fluid in its intended application or point of measurement.

In U.S. Pat. No. 7,007,546 the present inventor detailed a method for measuring the viscosity of a fluid at a selected shear rate, and methods for characterizing characteristics of a fluid by measuring the viscosity of the fluid at selected shear rates. This is achieved by utilizing an Acoustic Wave Device (AWD). The method for measuring viscosity at a desired shear rate utilizes an AWD sensor and an estimate of the shear rate at which the sensor operates, and then modifying the input power level to obtain the desired shear rate. It utilizes measurements of both the input and output power levels and the selection of an input power level by an algorithm. The method of characterizing the fluid characteristics include feeding different levels of power to the sensor and measuring fluid viscosities at the differing power levels. The present invention represents an improvement to the method described in the '546 patent.

SUMMARY OF THE INVENTION

The present invention utilizes an Automatic Level Control (ALC) circuit as the preferred method of controlling the input power level to the sensor. The ALC circuit may be analog, digital or a combination thereof.

Thus, in its most basic embodiment the present invention provides an apparatus for controlling the shear rate at which viscosity is measured, the apparatus utilizes an AWD sensor 10 having an input and an output, a controlled power source 20 coupled to the input of the sensor, an output power detector 25 coupled to the sensor output, for generating an output level signal representative of the output power. The output level signal is coupled to an input of an error measurement circuit 99 for producing an error signal reflective of the difference between the output power level and the set point. The error signal is used to control the input power to the sensor.

In a more preferred embodiment, the present invention further comprises an input power detector for generating an input power signal, and an averaging circuit coupled to the input level signal and to the output level signal and operative to generate an average signal therefrom, wherein the averaging signal is coupled to the input of error measuring circuit.

In certain embodiments, the invention assists in characterizing the fluid by measuring its viscosity at differing shear rates, wherein the ALC set point is variable, under manual or automatic control.

In a most preferred embodiment, there is provided a sensor wherein the controlled power source is a controlled gain amplifier having a control input, an input and an output, the amplifier input is coupled to the sensor output, and the amplifier output is coupled to the sensor input, and the control input being coupled to the error signal. Those skilled in the art will recognize that the controlled gain amplifier may comprise several components and amplifiers and that the control input may be achieved by controlling the amplifier gain by setting an operating point, such as by way of example by a transistor or a second amplifier. Thus, the term controlled power source should be construed to extend to any power source suitable for driving a sensor at varying power level responsive to a circuit input which adjusts the power level, and the term controlled gain amplifier should be construed to any number of member component in a circuit having input which is reflected at the output, and having a control input which electrically varies the gain between the input and the output.

Further preferably, the error measurement circuit is a comparator, and in one preferred embodiment, the comparator is a digital comparator.

In another aspect of the invention there is provided a method for controlling the shear rate at which viscosity of a fluid is measured by an AWD sensor coupled thereto, the method comprises the steps of feeding input power to the sensor via a controlled power source, measuring the output power from the sensor to produce an output level signal, and utilizing the output level signal to adjust the input power level by controlling the output of the controlled power source. Preferably the method further comprises the step of comparing, directly or indirectly, the output level signal against a set point and generating an error signal, and utilizing the error to control the input power level.

In a more preferred embodiment, the method further comprises the step of measuring the input power level, averaging the input power level and the output power level to produce an average signal, and utilizing the average signal to control the input power level to the sensor. It is noted that by doing so, the measured output power level signal is utilized indirectly to control the input power level, as described above.

More preferably, the controlled power source is a controlled gain amplifier, having an input coupled to the input of the sensor, and an input coupled to the output of the sensor, and a control input coupled to the error signal of either the output power level signal, or the average of the input level signal and the output power signal, via an error signal circuit.

A further method is provided to characterize the measured fluid by sequentially adjusting the set point to a plurality of values, and measuring the viscosity of the fluid for at least a subset of the plurality of values. This enables the creation of a table comprising the viscosity measurements and the values, or shear rate represented by those values, or similar representations that provide characteristic behavior of the fluid viscosity versus shear rates.

SHORT DESCRIPTION OF DRAWINGS

The invention will be better understood with the aid of the enclosed drawings in which.

DETAILED DESCRIPTION

In these specifications, an acoustic wave device is considered a device comprising a crystalline material having a plurality of electrodes, and that in response to electrical power presented between at least a pair of these electrodes, provides a corresponding movement of the crystal face, and conversely, generates an electrical signal in the electrodes in response to power applied to the crystal face.

Figure 1:
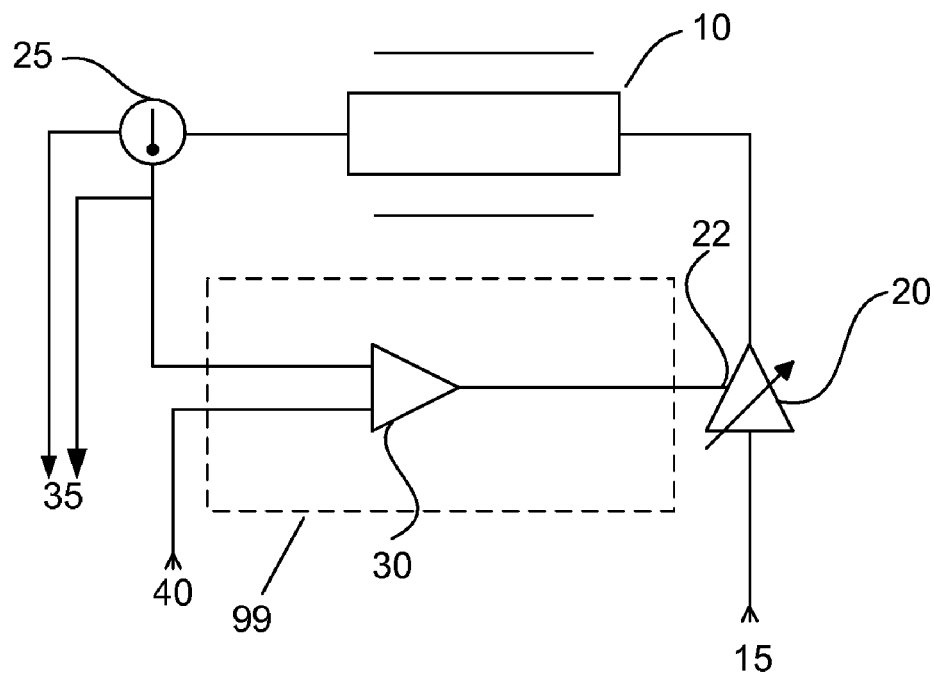
FIG. 1 depicts a simplified schematic diagram of a preferred embodiment of the apparatus, where the ALC is responsive to output power.

FIG. 1 depicts a simple embodiment of the invention. A controlled power source 20 is coupled to the input of AWD sensor 10. Those skilled in the art will recognize that such a power source may be any circuit or device that controls the feeding of input energy 15 to the sensor responsive to control input 22. Thus, by way of example the controlled power source may be a controlled gain amplifier, an AC or RF power source, a modulator, and the like.

The output power level of sensor 10 closely approximates the sensor input power level minus the power that was transferred to the liquid under measurement and a term related to electrical mismatch losses that is known. This output power is measured by an output power detector 25. Most AWD sensors are driven by RF power, and therefore a common method of measuring output power utilizes an RF diode detector, as known. The most preferred embodiment uses a diode detector as disclosed in U.S. Pat. No. 6,825,715 titled 'high efficiency temperature compensated diode detector' to the present inventor. However any power detection method may be used.

In certain embodiments, the output of output power detector 25, sometimes coupled with a sampling of the sensor output signal itself, forms the output 35 of the sensor assembly. While the power output level signal is a clear indication of the insertion loss of the sensor, it is sometimes desired to analyze other parameters, such as frequency shift, output signal phase, and the like, to obtain additional information about the measurements. In some embodiments, only the output of the sensor is considered to be the sensor assembly output.

The measurement obtained by output power detector 25 is fed to an error measurement circuit 99. A simple form of error measurement circuit comprises a comparator 30. The comparator may be embodied in analog or digital fashion or a combination thereof, and is operable to produce an error signal reflective of the error between a set point signal 40 and the measured power. The error signal, i.e. the comparator output, is fed to the control input 22 of controlled power source 20. The set point 40 may be fixed, or variable by any convenient manner. Examples of controlling the set point are the like of a user manual control, or automatically such as by a pre-selected set of set points, a computer, or a signal generator controlled set points, and the like.

Those skilled in the art will recognize that the circuit described herein forms an Automatic Level Control (ALC), also known as an Automatic Gain control (AGC) circuit where the power output of the sensor controls the input power. Clearly, if the output power is kept at a known level, the total input power provides a measurement of the power insertion loss to the device and may itself provide an output for the sensor assembly. Similarly measuring the error signal may provide an indication useful as a sensor assembly output. Thus the shown outputs 35 extend to any one output or any combination of the outputs described herein.

Figure 2:
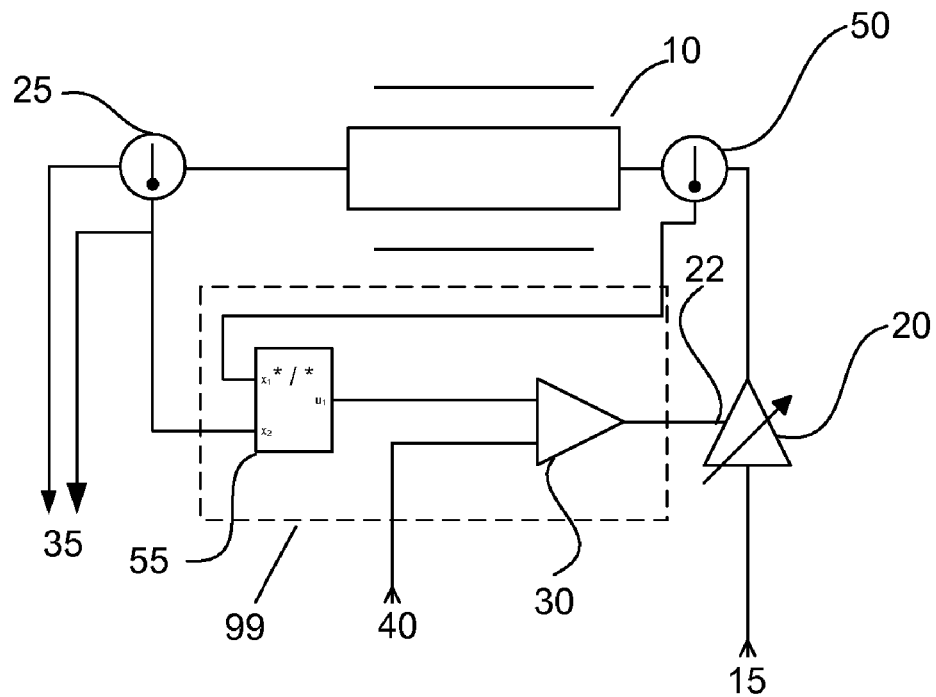
FIG. 2 depicts a simplified schematic diagram where the ALC is responsive to both input and output power.

The potential variations in input impedance of the AWD 10 and variations in saturated power of amplifier 20 lead to error terms that are readily corrected by differentially measuring the output power with respect to the input power. Furthermore, the shear rate varies slightly along the length of the AWD due to the distributed losses and knowledge of both input and output power leads to better understanding of the average and the range of the power and thus the shear rate. These factors dictate the desirability of measuring the sensor input power as well as the output power, and using the combined signal as input to the error measurement circuit 99. It is noted that this embodiment also uses the sensed output power level, but in combination with other elements. Thus, as shown in FIG. 2, an input power detector 50 is used to obtain the input power level signal. Any convenient manner combining the input power level signal and the output power level signal may be used. The most preferred being an average of the input and output level signals, but the combination may be carried out by weighted averaging, multiplication, and the like, which can be carried out by analog or digital manner. For clarity, the mixing of the input power level and the output power level signals shall be referred to as averaging. The preferred embodiment calls for the signal averaging to be performed by averaging circuit 55, the construction of which will vary in accordance with the desired function, but will be clear to the skilled engineer, and may range from simple resistive summation, to time constant circuit, or any number of analog or digital embodiments including non-linear equations or circuits. The averaging circuit 55 output is then compared to the set point 40 by comparator 30, which in turn generates the error signal that is fed to the control circuit input 22 of the controlled power source 20. This implementation has the advantage that the shear rate is controlled in real time and is compensated at least over small variations in viscosity. When used in conjunction with the original approach of the '576 patent, in which data is measured and a set point is manually or computationally altered, the ALC circuit will provide short term compensation and will reduce variability within a measurement while the original algorithm will provide long-term analytical control of the shear rate. When used as the sole method of controlling the shear rate, the ALC circuit offers a useful real-time compensation of the shear rate in a simplified sensor over variations in sample viscosity. This approach has significant advantages for in situ process control requirements, which represent the most significant growth area of applications.

Figure 3:
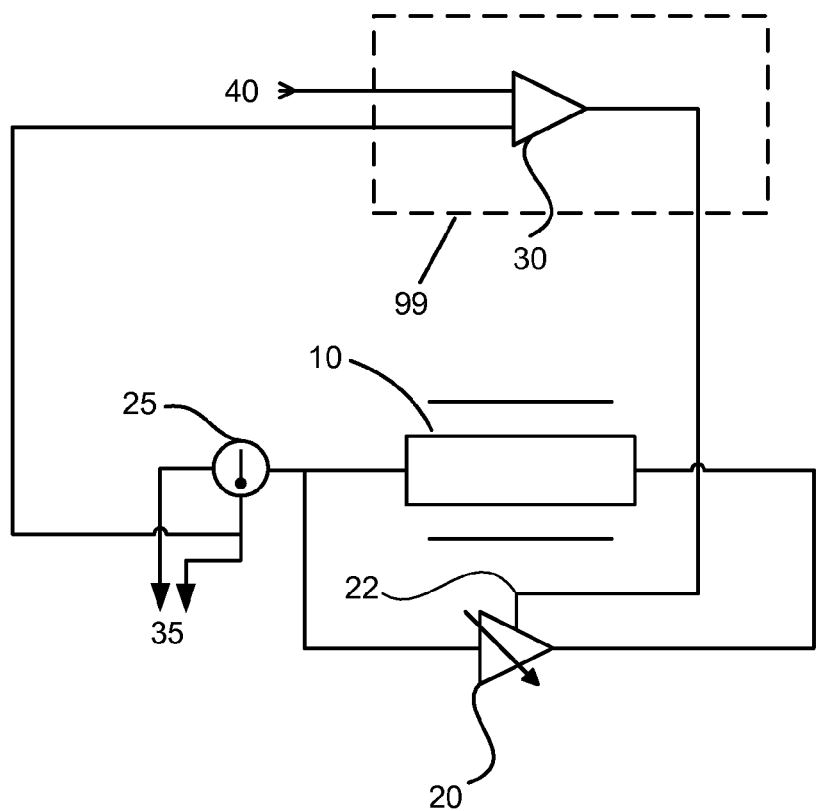
FIG. 3 depicts an embodiment of the invention with output power controlling the gain of an amplifier forming an oscillator with the AWD.
Figure 4:
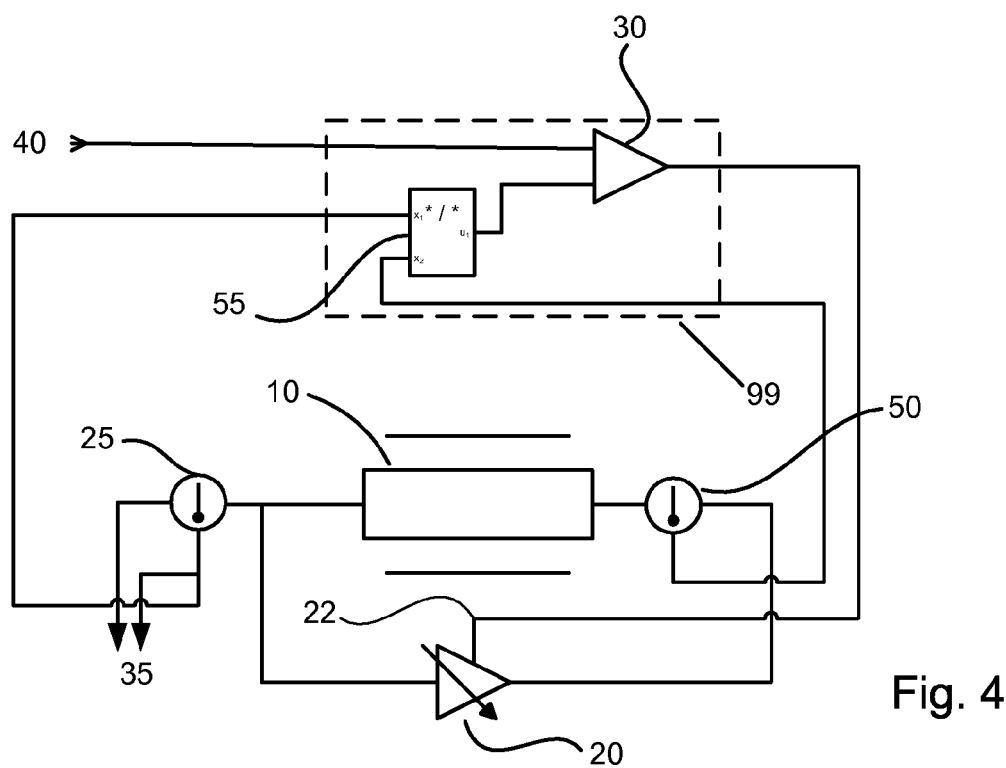
FIG. 4 depicts an embodiment of the invention with output power and the input power control the gain of an amplifier forming an oscillator with the AWD.

FIGS. 3 and 4 depict a more preferred embodiment. FIG. 3 is a simplified schematic diagram of an apparatus which measures only the sensor output power to control the input power level and FIG. 4 depicts an embodiment in which both the input power level and the output power level are measured.

The components relating to measurement of the sensor output power by output power detector 25 and the creation of an error signal by error measurement circuit 99 are similar to those described for FIG. 1. However, in this embodiment, the controlled power source 20 is an amplifier coupled to the output of sensor 10. Those skilled in the art will easily recognize that as long as the amplifier could provide sufficient gain, the circuit forms an oscillator. Thus, the desired result of setting the shear rate at which the viscosity measurement is performed is achieved by controlling the set point 40 in a similar way to the operation of the circuit depicted FIG. 1 or 2. Further similarly, measuring the input power by input power detector 50 and averaging the input and output power level signals by averaging circuit 55, provides a stable operating point for the circuit.

Figure 5:
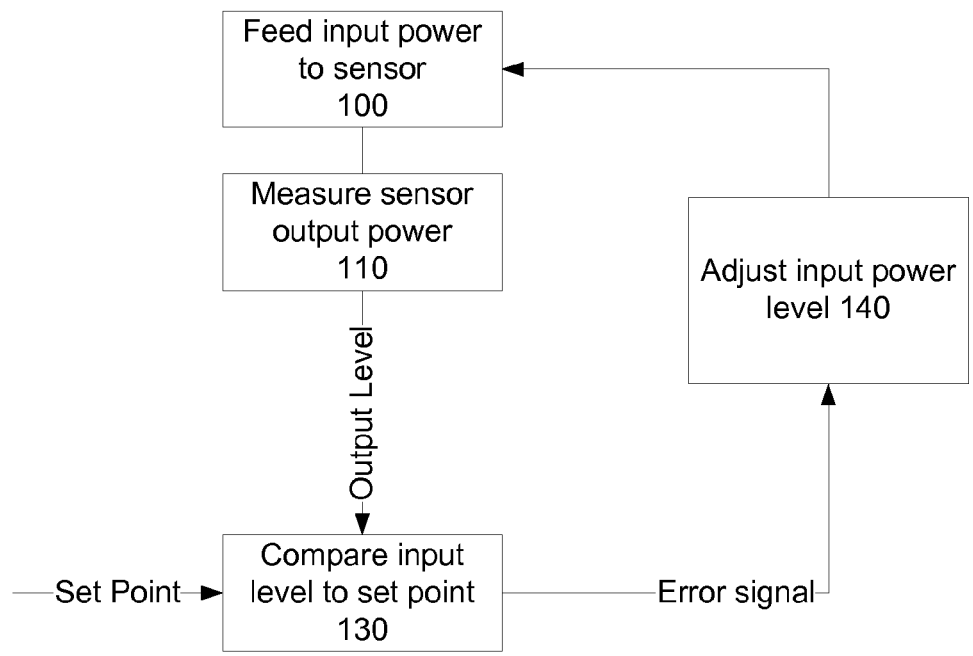
FIG. 5 is a block diagram showing flow of a preferred embodiment of a method aspect of the present invention.
Figure 6:
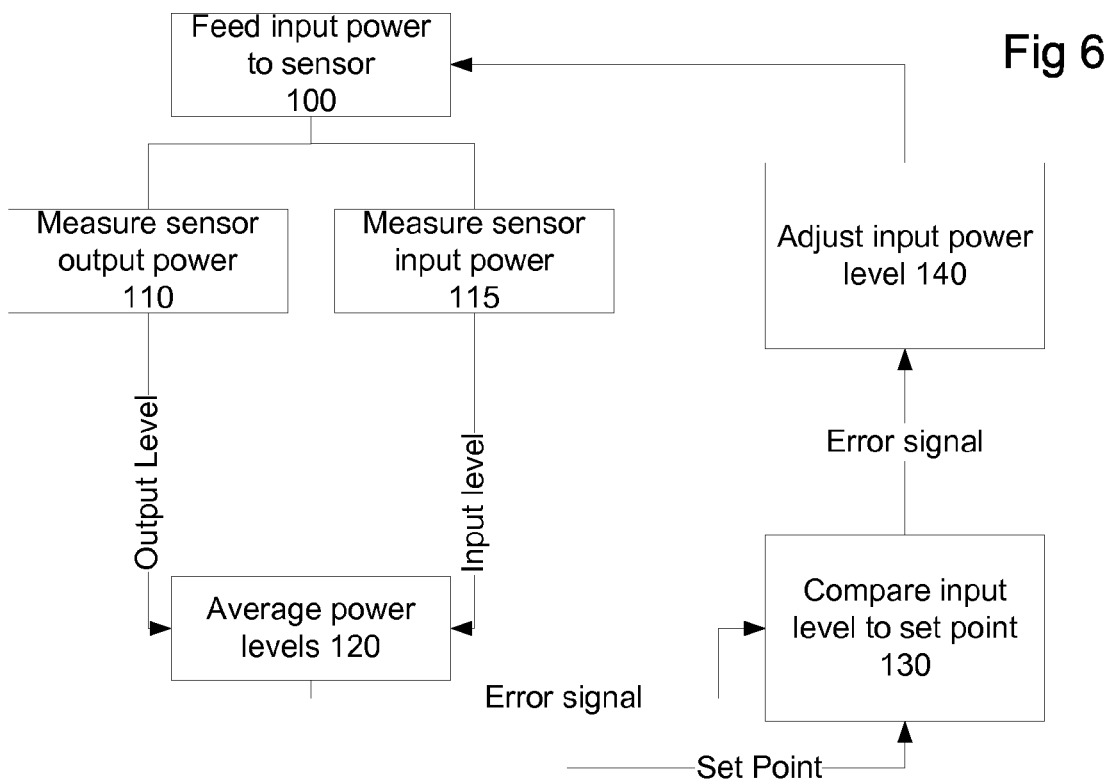
FIG. 6 is a block diagram showing flow of an embodiment which includes averaging of input and output power into the sensor.

FIG. 5 is a block diagram depicting the flow of a method for controlling the shear rate at which viscosity of a fluid is measured by an AWD sensor coupled thereto. The method comprises the steps of feeding input power to the sensor 100 via a controlled power source, measuring 110 the output power from the sensor to produce an output level signal, and comparing 130 the output level signal to a set point, the comparison results in an error signal. The error signal is used to adjust 140 the input power to the sensor. As shown in FIG. 6, the more preferred embodiment calls also for the steps of measuring 115 the input power to the sensor, and averaging 120 the input power level signal and the output power level signal to produce an averaged signal. The averaged signal is then compared 130 with the set point and the input power level is adjusted 140 as described above.

FIG. 6 depicts an analogous flow to that depicted in FIG. 5, where the input and output power are measured.

The set point may be fixed, or preferably adjustable. Adjusting the set point may be done manually, but more preferably is automatic. Various set points may be set in order to determine fluid characteristics. In this preferred embodiment, a computer (not shown) is used to sequentially adjust the set point to varying values, and measure the viscosity. Thus, a characterizing set of viscosities may be created, each taken at a different shear rate, which affords better knowledge of the fluid.

Figure 7:
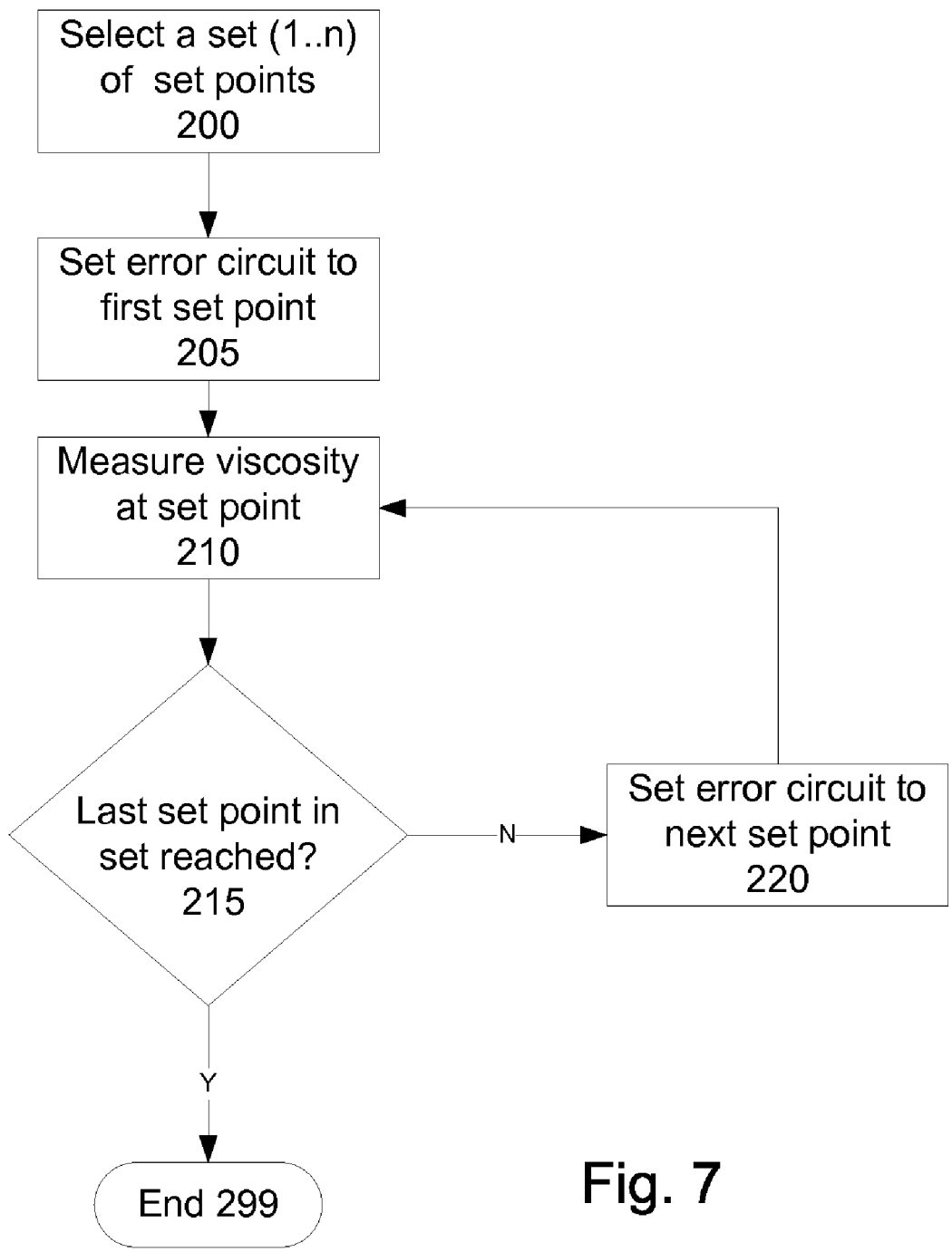
FIG. 7 is a flow diagram showing the aspect of creating a characterization of the fluid by measurements of viscosity at varying shear rates.

The process of characterizing the fluid is shown in a simplified block diagram of FIG. 7. A set (1. . . nl) of set points is selected 200. The set points represent various shear rates as desired, and the selection may be made at any desired time, such as a predetermined set, or dynamically during measurements operation. The first selected value is set 205 as the set point, thus in practical terms setting a first shear rate value at which the fluid viscosity is measured 210. A test is performed 215 to determine if the set point is the last point of the selected set (1. . . n), the process can terminate 299, or be preformed again. If more set points are in the set, the error circuit set point is set 220 to the next selected set point.

It will be appreciated that the invention is not limited to what has been described hereinabove merely by way of example. While there have been described what are at present considered to be the preferred embodiments of this invention, it will be obvious to those skilled in the art that various other embodiments, changes, and modifications may be made therein without departing from the spirit or scope of this invention and that it is, therefore, aimed to cover all such changes and modifications as fall within the true spirit and scope of the invention, for which letters patent is applied.

What is claimed is:

1. An apparatus for controlling the shear rate at which viscosity is being measured, the apparatus utilizing an Acoustic Wave Device (AWD) sensor having an input and an output, the apparatus comprising:
   a controlled power source having an output coupled to said sensor input;
   an input power detector coupled to said sensor input, for generating an input power level signal representative of said sensor input power;
   an output power detector coupled to said sensor output, for generating an output level signal representative of said sensor output power;
   an error measurement circuit having an input, for producing an error signal reflective of the difference between at least said output power level signal and a set point;
   an averaging circuit coupled to said input power level signal and to said output power level signal, and operative to generate an average signal therefrom;
   wherein said average signal is coupled to said input of error measurement circuit; and
   wherein said error signal is used to control the input power to said sensor via said controlled power source.

2. An apparatus for controlling the shear rate at which viscosity is being measured as claimed in claim 1, wherein said set point is variable, under manual or automatic control.

3. An apparatus for controlling the shear rate at which viscosity is being measured as claimed in claim 1, wherein:
   said controlled power source comprises a controlled gain amplifier having a control input, an input and an output;
   said amplifier input coupled to said sensor output;
   said amplifier output coupled to said sensor input; and
   said control input coupled to said error signal.

4. An apparatus for controlling the shear rate at which viscosity is being measured as claimed in claim 3, wherein said control input is controlling the amplifier power level at which the sensor is driven thereby setting an operating point.

5. An apparatus for controlling the shear rate at which viscosity is being measured as claimed in claim 1, wherein said error measurement circuit is a comparator.

6. An apparatus for controlling the shear rate at which viscosity is being measured as claimed in claim 5, wherein said comparator is a digital comparator.

7. An apparatus for controlling the shear rate at which viscosity is being measured as claimed in claim 5, wherein said comparator is an analog comparator.

8. A method for controlling the shear rate at which viscosity of a fluid is measured by an Accoustic Wave Device (AWD) sensor coupled thereto, the method comprises the steps of:
 feeding input power to said sensor via a controlled power source;
 measuring said sensor's input power level for producing an input power level signal;
 measuring the output power from said sensor to produce an output power level signal;
 averaging said input power level signal and said output power level signal to produce an average signal; and
 utilizing said average signal to adjust said sensor input power level by controlling the output of said controlled power source.

9. A method for controlling the shear rate at which viscosity of a fluid is measured as claimed in claim 8, wherein said controlled power source comprises a controlled gain amplifier.

10. A method for controlling the shear rate at which viscosity of a fluid is measured as claimed in claim 8, further comprising the step of varying said set point.

11. A method for controlling the shear rate at which viscosity of a fluid is measured as claimed in claim 10, further comprising the steps of:
 sequentially adjusting said set point to a plurality of values;
 measuring the viscosity of said fluid, for at least a subset of said plurality of values; and
 creating a data set comprising said viscosity measurements and said values, or values representative thereof.

12. An apparatus for controlling the shear rate at which viscosity is being measured, the apparatus utilizing an Acoustic Wave Device (AWD) sensor having an input and an output, the apparatus comprising:
 a controlled power source having an output coupled to said sensor input;
 an output power detector coupled to said sensor output, for generating an output level signal representative of said sensor output power;
 an input power detector coupled to said sensor input, for generating an input power level signal representative of said sensor input power;
 an averaging circuit coupled to said input power level signal and to said output power level signal, and operative to generate an average signal therefrom; and
 an error measurement circuit coupled to said average signal, for producing an error signal reflective of the difference between at least said output power level signal and a set point;
 wherein said error signal is used to control the input power to said sensor via said controlled power source.

13. An apparatus for controlling the shear rate at which viscosity is being measured as claimed in claim 12, wherein:
 said controlled power source comprises a controlled gain amplifier having a control input, an input and an output;
 said amplifier input coupled to said sensor output;
 said amplifier output coupled to said sensor input; and
 said control input coupled to said average signal.

14. An apparatus for controlling the shear rate at which viscosity is being measured as claimed in claim 12, wherein said error measurement circuit is a comparator.

* * * * *